(12) United States Patent
Grimm (10) Patent No.: US 9,019,307 B1
(45) Date of Patent: Apr. 28, 2015

(54) AUTOMATED WARNING SYSTEM AND METHOD FOR USE WHEN EVALUATING ACCEPTABLE DOSAGE RANGES FOR RADIATION TREATMENTS OF BODY TISSUE

(71) Applicant: Jimm Grimm, Huntingdon Valley, PA (US)

(72) Inventor: Jimm Grimm, Huntingdon Valley, PA (US)

(*) Notice: Subject to any disclaimer, the term of this patent is extended or adjusted under 35 U.S.C. 154(b) by 2 days.

(21) Appl. No.: 13/916,577

(22) Filed: Jun. 13, 2013

Related U.S. Application Data (63) Continuation-in-part of application No. 12/983,434, filed on Jan. 3, 2011, now abandoned.

(60) Provisional application No. 61/335,351, filed on Jan. 6, 2010.

(51) Int. Cl.
*A61N 5/10* (2006.01)
*A61N 5/06* (2006.01)

(52) U.S. Cl.
CPC .............. *A61N 5/103* (2013.01); *A61N 5/1031* (2013.01); *A61N 2005/0627* (2013.01)

(58) Field of Classification Search
None
See application file for complete search history.

(56) References Cited

U.S. PATENT DOCUMENTS

| 6,560,311 B1* | 5/2003 | Shepard et al. | 378/65 |
| 2005/0111621 A1* | 5/2005 | Riker et al. | 378/65 |

* cited by examiner

*Primary Examiner* — David H Chu
(74) *Attorney, Agent, or Firm* — LaMorte & Associates, P.C.

(57) ABSTRACT

A computer-based system and method that provides an automatic warning when a planned dose of radiation exceeds a predetermined safety limit. A tissue mass and surrounding healthy tissue is imaged to obtain imaged data. A dose volume histogram is generated that plots at least some of the imaged tissue versus proposed doses of radiation. The dose volume histogram presents a data curve when plotted. At least one dose tolerance limit is recalled from a reference database. The system computer analyzes the dose tolerance limits and compares this data to the data curve. The system computer determines if the data curve surpasses any selected dose tolerance limit at any point along the data curve.

14 Claims, 7 Drawing Sheets

AUTOMATED WARNING SYSTEM AND METHOD FOR USE WHEN EVALUATING ACCEPTABLE DOSAGE RANGES FOR RADIATION TREATMENTS OF BODY TISSUE

RELATED APPLICATIONS

The present application is a continuation-in-part of U.S. patent application Ser. No. 12/983,434, filed Jan. 3, 2011, which claims priority of U.S. Provisional Patent Application No. 61/335,351, filed Jan. 6, 2010.

BACKGROUND OF THE INVENTION

1. Field of the Invention

In general, the present invention relates to systems and methods that warn medical personnel if an improper radiation dosage has been selected for a particular patient. More particularly, the present invention relates to software applications that provide graphical indications of radiation dose ranges and warnings of potential dangers.

2. Prior Art Description

There are many medical conditions that can be treated with radiation therapy. However, one of the most important applications of radiation therapy is its use in treating cancer inside the body. If cancer cells can be located within the human body, then those cancer cells can be targeted with beams of radiation. The radiation carries enough energy to kill the cancer cells as the radiation impinges upon the cancer cells. In this manner, cancer cells can be killed deep within tissue masses.

The radiation beams begin at different physical points. Each individual radiation beam has a low dose that is insufficient to damage cells by itself. In this manner, the beams of radiation can reach the cancer cells without damaging healthy tissue along the path. The multiple beams of radiation all converge at the point of the cancer cells. The combined dose from the multiple beams of radiation then becomes sufficient to kill the cancer cells.

A problem associated with radiation therapy is that the level of radiation increases as the beams of radiation approach the treatment area. Consequently, the tissue surrounding the tumor is subjected to significant levels of radiation. Likewise, the tissue along each path of the radiation beams is also subjected to some radiation dose.

No two cancers are alike. Each cancer patient has cancer cells that are unique in location and mass to that patient. As such, the best way to direct beams of radiation onto cancer cells has become a complicated science. Physicians and dosimetrists must determine where to position the beams of radiation during radiation therapy in order to have the maximum effect on the cancer cells and the minimal effect on surrounding healthy tissue. Doctors and dosimetrists also try to avoid radiation dose to critical organ tissue, provided that tissue is healthy.

In the prior art, the manner in which a physician or dosimetrist plans a course of radiation therapy is a multi-step process. In the first step, the physician pinpoints the exact location of the cancer cells to be targeted. This is traditionally done using three-dimensional body imaging equipment, such as an MRI scan, a CAT scan, a PET scan or the like. Once the physician locates the target cancer cells, the physician/dosimetrist enters the outlines of the patient's anatomy into a computer that is running a treatment planning system. The treatment planning system runs software that computes a dose for all the anatomical structures that were entered into the system. The doses of all entered anatomical structures are then summarized graphically in the form of a dose volume histogram (DVH). The use of a treatment planning system to create a dose volume histogram is shown in U.S. Pat. No. 6,560,311 to Shepard, entitled Method For Preparing A Radiation Therapy Plan.

The physician/dosimetrist utilizes the dose volume histograms to evaluate the dose distribution of radiation in and around the targeted cancer cells. The physician/dosimetrist can alter the dose, position, and direction of the various radiation beams to develop a plan that will kill the targeted cancer cells, yet minimize dose to surrounding tissue, especially critical organ tissue. In the last step, the radiation equipment is programmed to the settings developed using the treatment plan. The equipment is then ready for use on the patient.

It will be understood that the dose volume histogram generated for a particular cancer in a particular patient is unique. In the prior art, systems that are used to produce does volume histograms do not have ability to also chart safety limit information onto the dose volume histograms being produced. As such, a physician/dosimetrist must cross-reference the graphical information presented on the dose volume histogram with the non-graphic empirical data of radiation exposure charts and dose tolerance limits in order to determine if any safety threshold is being approached. Furthermore, since the prior art systems that generate the dose volume histogram do not reference safety data, such systems lack the ability to warn about a potentially unsafe condition.

Many prior art systems use treatment planning constraints for an algorithm to optimize the dose. However, due to conflicting constraints of the tissue mass and surrounding normal tissue, the actual resulting dose is usually either above or below the constraint. When radiation plans do not meet the desired doses, good dosimetrists develop skill at pre-emptively setting the treatment planning constraints to fictitious values to repeatedly goad the algorithm into providing better results than it normally could. The constraints given to the planning system then, have little to do with the actual human radiation dose tolerance limits, and these prior art systems do not evaluate the safety of the actual planned doses as compared to published dose tolerance limits.

A need therefore exists for a system and method that can actively inform a physician and/or dosimetrist that the settings selected for the radiation therapy surpass safe levels for any region of healthy tissue along the various radiation beam paths. This need is met by the present invention as described and claimed below.

SUMMARY OF THE INVENTION

The present invention is a computer-based system and method that provides an automatic warning when a planned dose of radiation exceeds a predetermined safety limit. In this manner, more effective and safe radiation treatment plans can be more rapidly produced.

In accordance with the system and method, a tissue mass is imaged to obtain imaged data. The imaged data identifies abnormal tissue that requires radiation therapy and normal tissue that the radiation therapy should attempt to avoid. A system computer is utilized that has access to reference databases. The reference databases contain published dose tolerance limits from the scientific literature.

A dose volume histogram is generated that plots at least some of the imaged data versus proposed doses of radiation. The dose volume histogram presents a data curve when plotted. At least one dose tolerance limit is recalled from the reference databases.

The system computer analyzes the dose tolerance limits that were recalled and compares this data to the data curve. The system computer determines if the data curve surpasses any selected dose tolerance limit at any point along the data curve. The system computer automatically generates a warning indicator should the data curve surpass any dose tolerance limit at any point along the data curve. In this manner, the present invention presents a graphical representation that enables a person to ascertain how a proposed radiation treatment plan compares to published dose tolerance limits. The system also provides a textual warning if any of the dose tolerance limits are surpassed in the radiation treatment plan.

BRIEF DESCRIPTION OF THE DRAWINGS

For a better understanding of the present invention, reference is made to the following description of an exemplary embodiment thereof, considered in conjunction with the accompanying drawings, in which.

DETAILED DESCRIPTION OF THE DRAWINGS

Although the present invention system and method can be used in the treatment of lung cancer, pancreatic cancer, breast cancer, and many other cancers, the exemplary embodiment illustrated shows the system being used to determine the proper radiation treatment plan for treating an unnamed mass of "tissue". This generic embodiment is selected in order to set forth an example that best illustrates the system and method of the invention. The illustrated embodiment, however, is merely exemplary and should not be considered a limitation when interpreting the scope of the appended claims.

Figure 1:
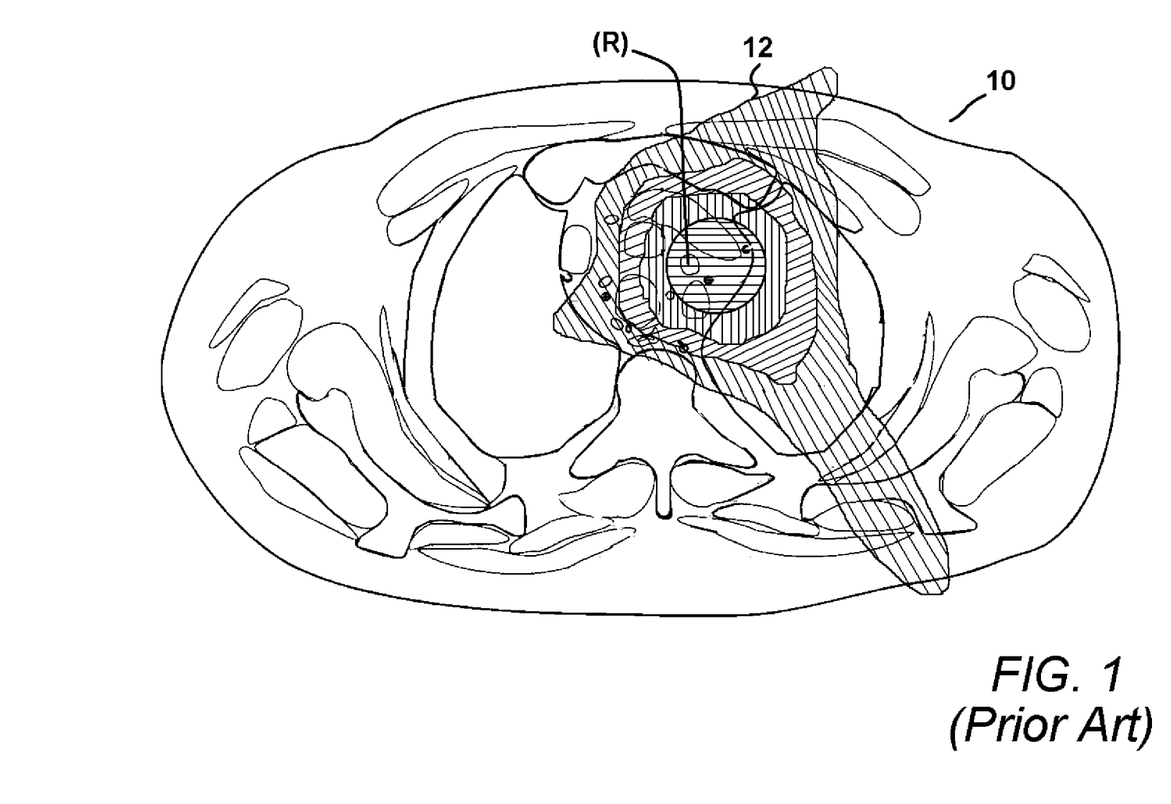
FIG. 1 is a prior art image of scanned body tissue having a radiation treatment plan superimposed over the scanned image.

Referring to FIG. 1, an image 10 available from prior art imaging equipment is shown. The image 10 shows a cross-section of the human body imaged by an imaging machine, such as an MRI scan, CAT scan or PET scan imager. Superimposed upon the image 10 is a radiation treatment plan 12. The radiation treatment plan 12 indicates the radiation dose levels to various tissue areas within the body for some predetermined operation settings of a radiation therapy machine. The image of FIG. 1 can be generated using available commercial treatment planning system software. Such prior art software also enables a physician or dosimetrist to select any one region (R) on the image 10. From all such regions (R) for a selected anatomical structure, a dose volume histogram can be produced. A dose volume histogram is later shown in FIG. 4. The dose volume histogram is a plot of tissue volume versus radiation dose, or alternatively, a plot of radiation dose versus tissue volume. The dose volume histogram can be expressed as a plot of $\vec{x}$, $\vec{y}$, where $\vec{x}$ is a vector of the range of doses in the plan, from the minimum dose to the maximum point dose, and $\vec{y}$ is the corresponding vector of the volume of the anatomical structure receiving each particular dose. The dose $\vec{x}$ and the volume $\vec{y}$ may be expressed in any applicable units, either absolute units or in normalized relative units.

Figure 2:
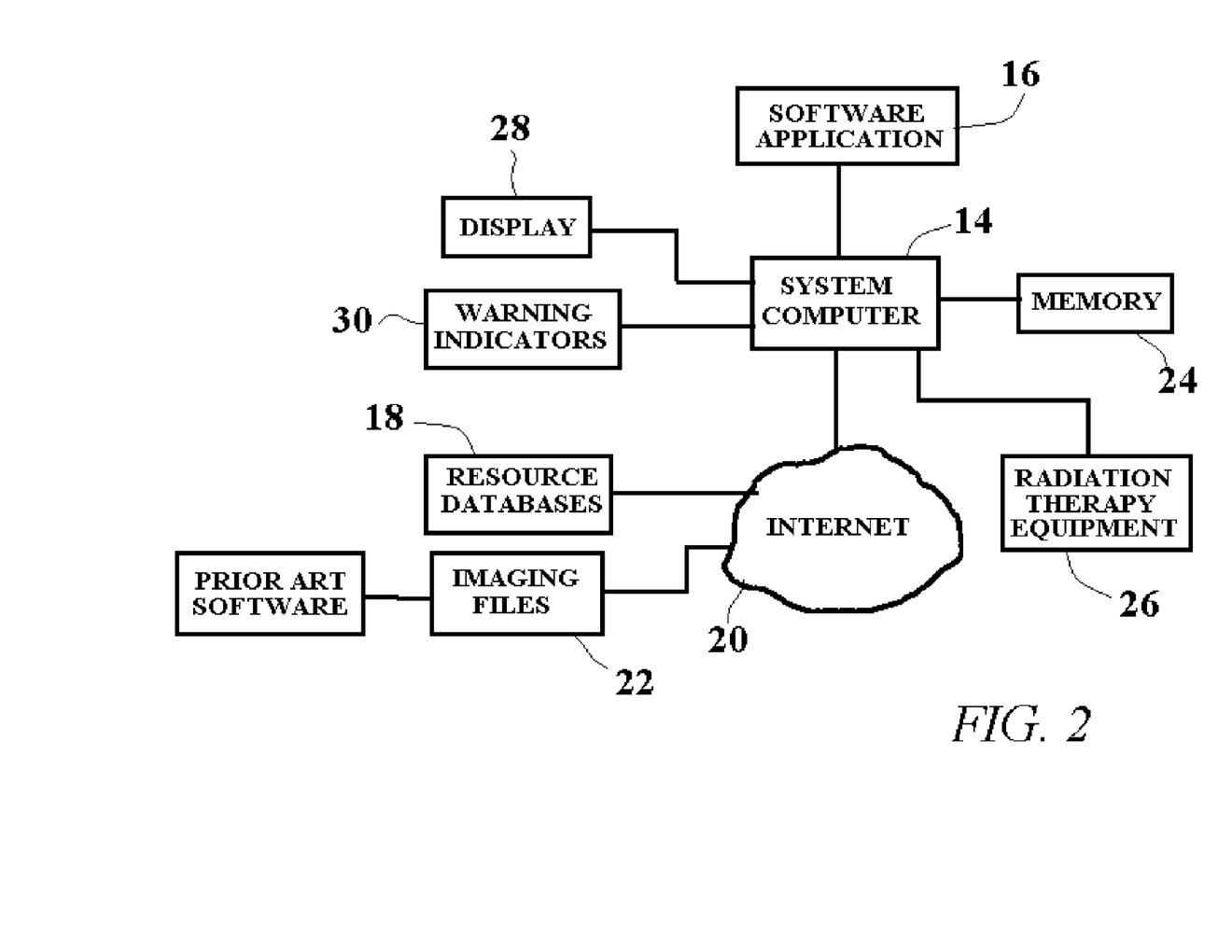
FIG. 2 is a schematic showing the major components of the present invention system.

The component requirements of the present invention are outlined with reference to FIG. 2. The system and method requires a system computer 14 that runs the software application 16 of the present invention. The system computer 14 has access to various resource databases 18, either directly or through a network connection such as the Internet 20. The system computer 14 also has access to the imaging files 22 produced by prior art software applications. The imaging files 22 contain the imaging data shown in FIG. 1 and the dose volume histogram data shown later in FIG. 4.

The resource databases 18 are used to determine radiation dosing limits for different cancers in different tissues. The system computer 14 may utilize a memory 24 that holds the current radiological dosage limits for various tissues. This memory 24 can be periodically updated using the resource databases 18. The resource databases 18 may contain dose tolerance limits for various tissue types that are periodically published in medical journals and technical papers. Likewise, there are many ongoing radiobiological studies that monitor and track the effects of various dose limits on various tissue types. The reference databases 18 may contain data from such clinical trials.

The system computer 14 is used to program operational instructions into radiation therapy equipment 26. The systems computer 14 may be integrated into the radiation therapy equipment 26. However, in most cases, the systems computer 14 will not transfer operational instructions to the radiation therapy equipment. As will later be explained, the present invention system creates graphical information that can be viewed at a display 28. Furthermore, the system can have auxiliary warning indicators 30 that are controlled by the system computer 14.

Figure 3:
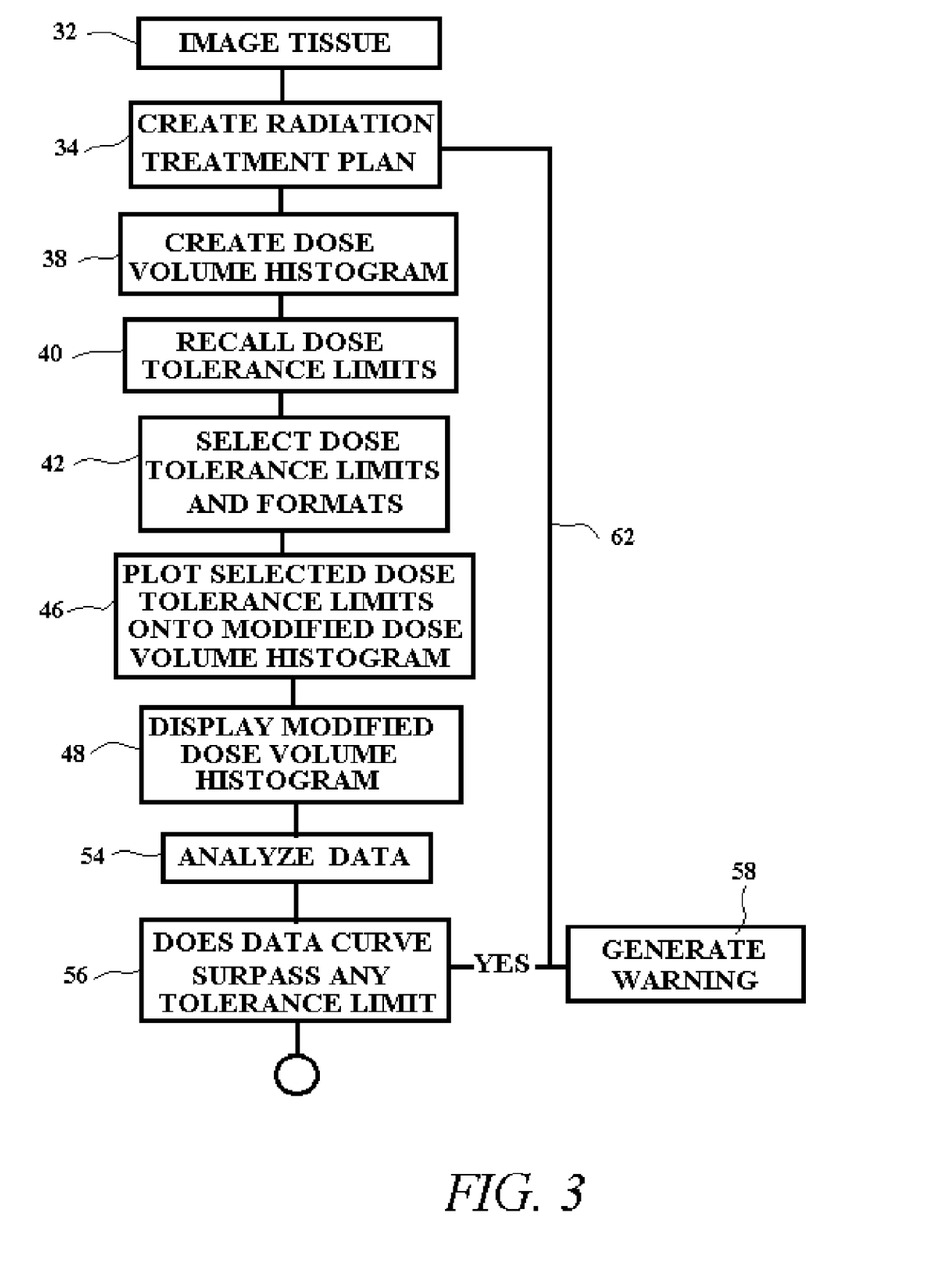
FIG. 3 is a flow chart illustrating the method of operation for the present invention.

Referring to FIG. 3, the operational methodology of the present invention is outlined. The initial steps have been previously described. The initial steps include the prior art steps of imagining tissue and inputting imaged tissue data into a treatment planning system. These steps are shown as Block 32 and Block 34.

Figure 4:
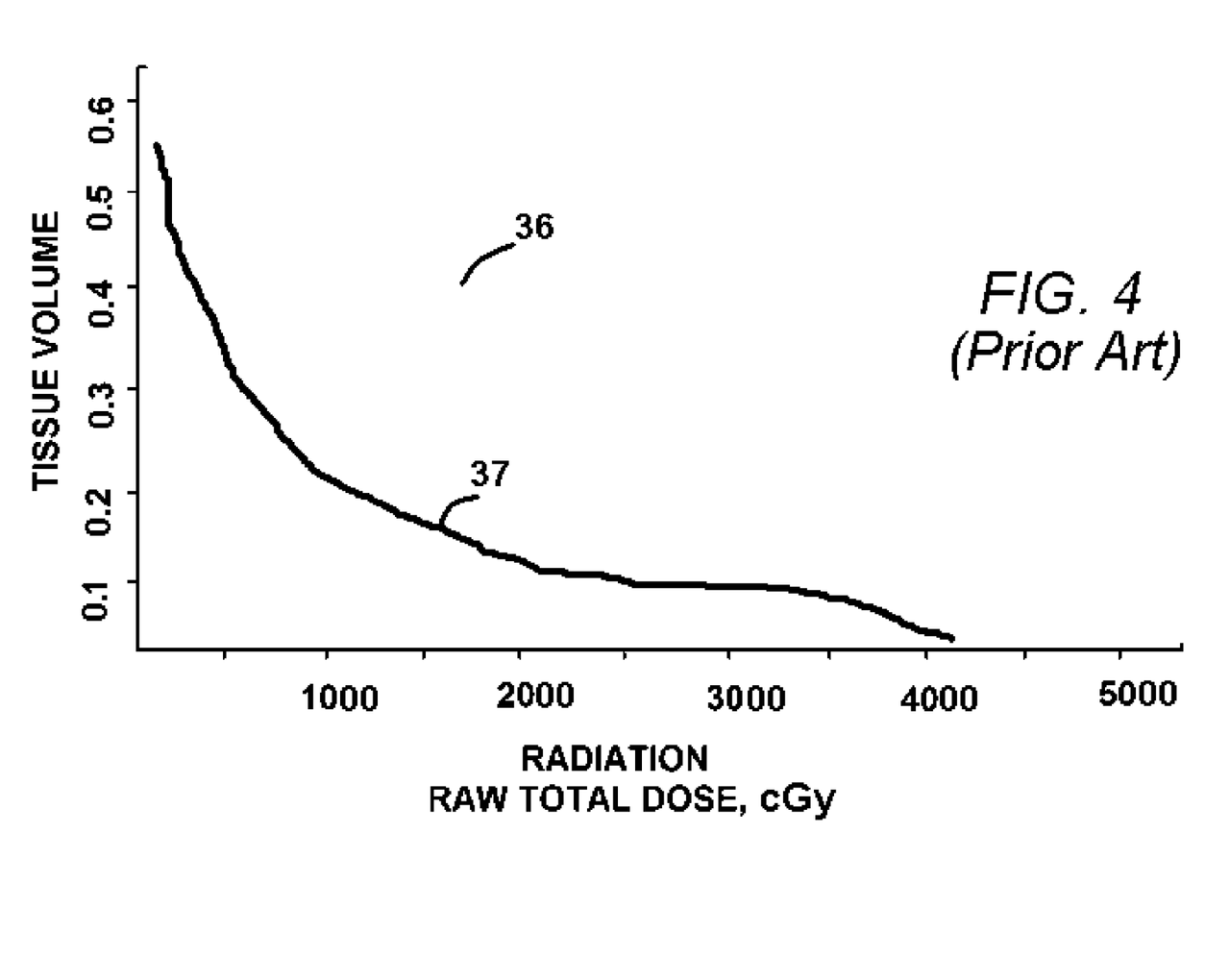
FIG. 4 is a prior art dose volume histogram.

Referring to FIG. 4 in conjunction with FIG. 3, it can be seen that data generated by the treatment planning system is used to generate a dose volume histogram 36. See Block 38. The dose volume histogram 36 plots tissue volume versus Raw Total Dose in cGy or other units. Since the dose volume histogram 36 is a graph, it presents a data curve 37.

Once the dose volume histogram 36 is created, the system can recall dose tolerance limits for the tissue represented within the dose volume histogram 36. See Block 40. As can be seen by Block 42, a physician can select different plotting formats for the dose tolerance limits. The first format choice indicates if volume $Y_A$ of the selected tissue area exceeds dose $X_A$. The second format choice indicates if only a certain percentage $Y_B$ of the selected tissue area exceeds dose $X_B$. The third format choice indicates if any tissue volume $Y_C=0$ (zero) of the selected tissue region exceeds dose $X_C$. This third format choice specifies the maximum point dose such that no volume (zero) of the tissue sample is allowed to exceed dose $X_C$. In all three formats, only $Y_i$ of a selected tissue sample may exceed dose $X_i$, where i is chosen from the three format sets and the units of $Y_i$ are volume or percent, and the unit of $X_i$ is dose.

Figure 5:
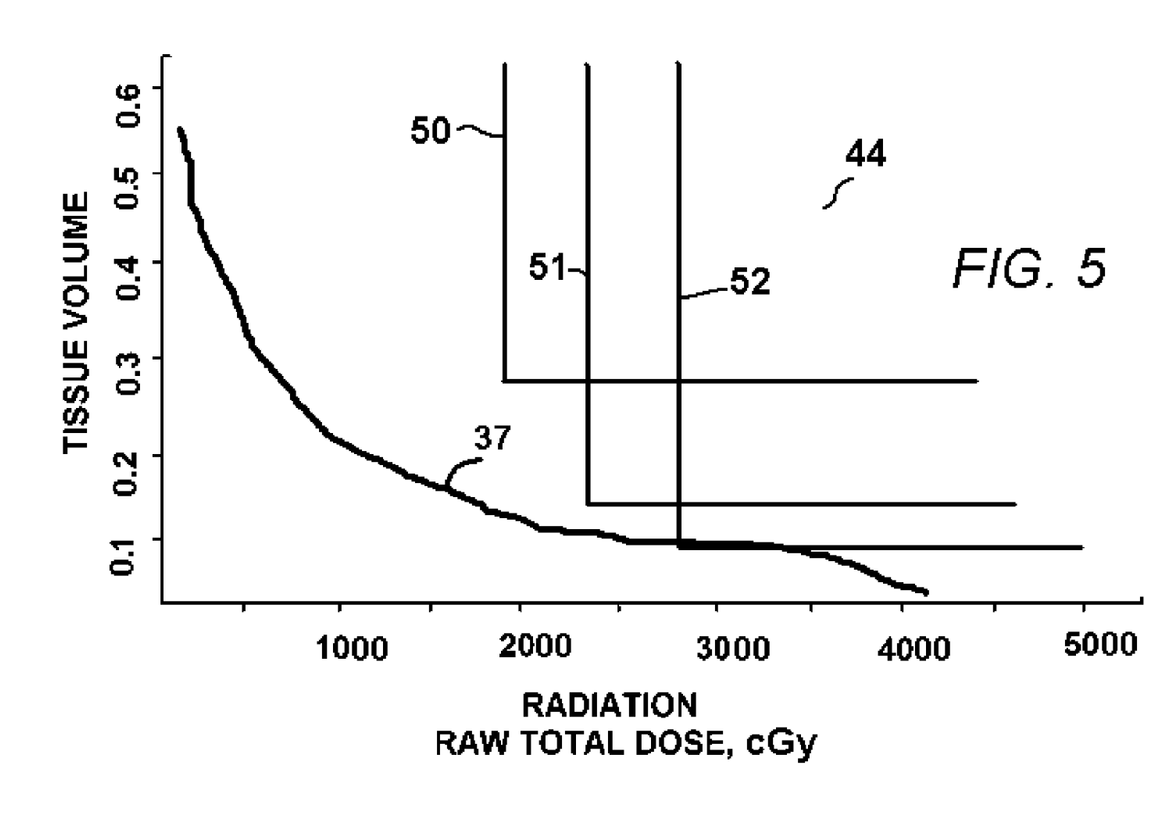
FIG. 5 is a modified dose volume histogram made in accordance with the present invention.

The data used to generate the dose tolerance limits are retrieved from either the memory 24 or the linked resource database 18. Referring to FIG. 5 in conjunction with FIG. 3, it will be understood that a modified dose volume histogram 44 is generated by plotting one or more of the dose tolerance limits 50, 51, 52 onto the same graph as the data curve 37 of the original dose volume histogram 36. See Block 46.

The modified dose volume histogram 44 is presented graphically to the physician/dosimetrist on the display 28. See Block 48. Furthermore, the software application 16 analyzes the data of the original dose volume histogram 36 with the data of the selected formats of the dose tolerance limits 50, 51, 52. See Block 54. If the data curve 37 of the original dose volume histogram 36 surpasses any of the dose tolerance limits 50, 51, 52, then a warning is automatically generated. See Block 56 and Block 58. In FIG. 5, it can be seen that the dose tolerance limits 50, 51, 52 can be in three selected formats. The data curve 37 of the original dose volume histogram 36 surpasses one of the dose tolerance limits 52 at point P. As such, a warning is automatically generated as shown in FIG. 6.

Figure 7:
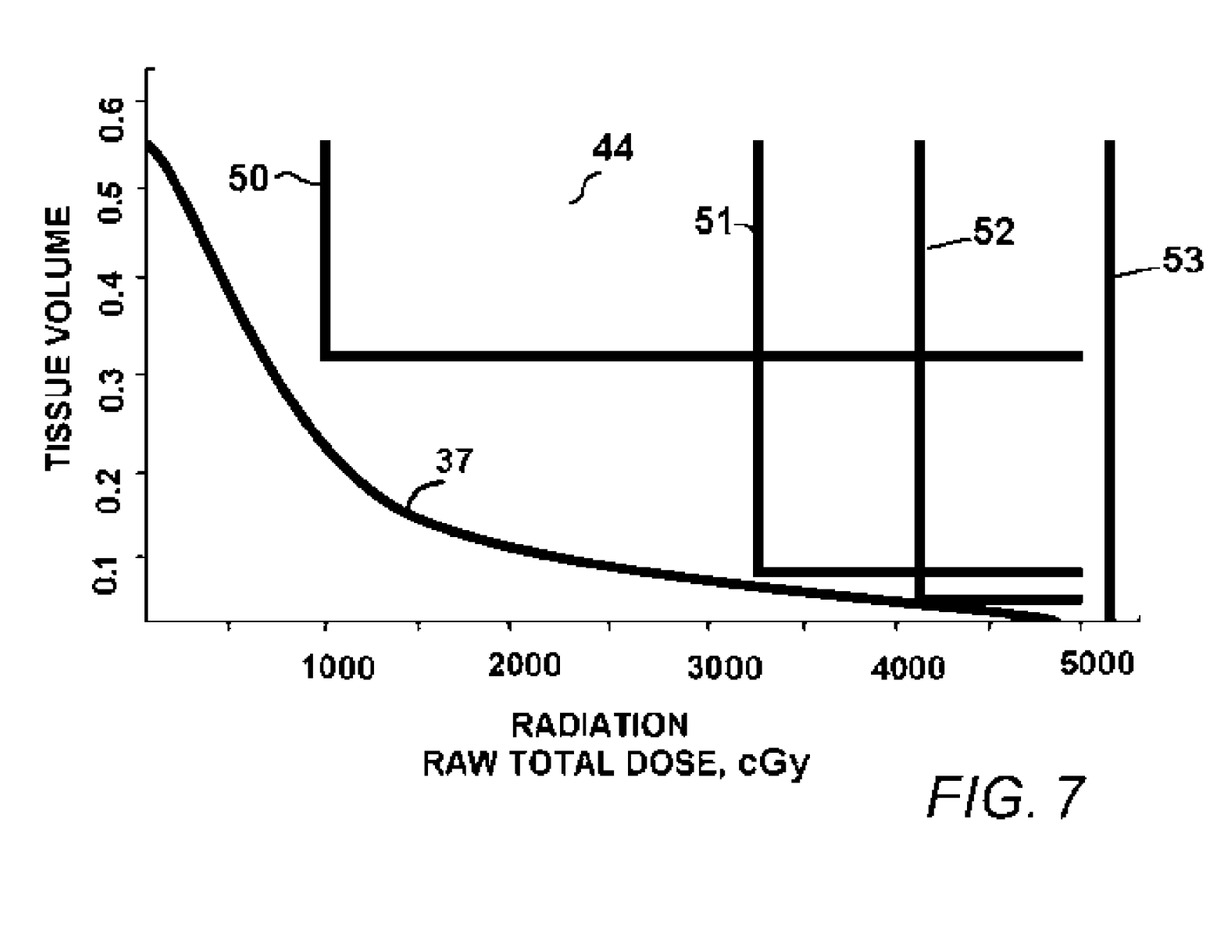
FIG. 7 shows an ideal example where the modified dose volume histogram is just meeting the multiple overlaid dose tolerance limits.

Conversely, when as in FIG. 7 for the ideal example modified dose volume histogram 44, the data curve 37 of the original dose volume histogram 36 does not exceed any of the dose tolerance limits 50-53, no warnings are displayed.

Figure 6:
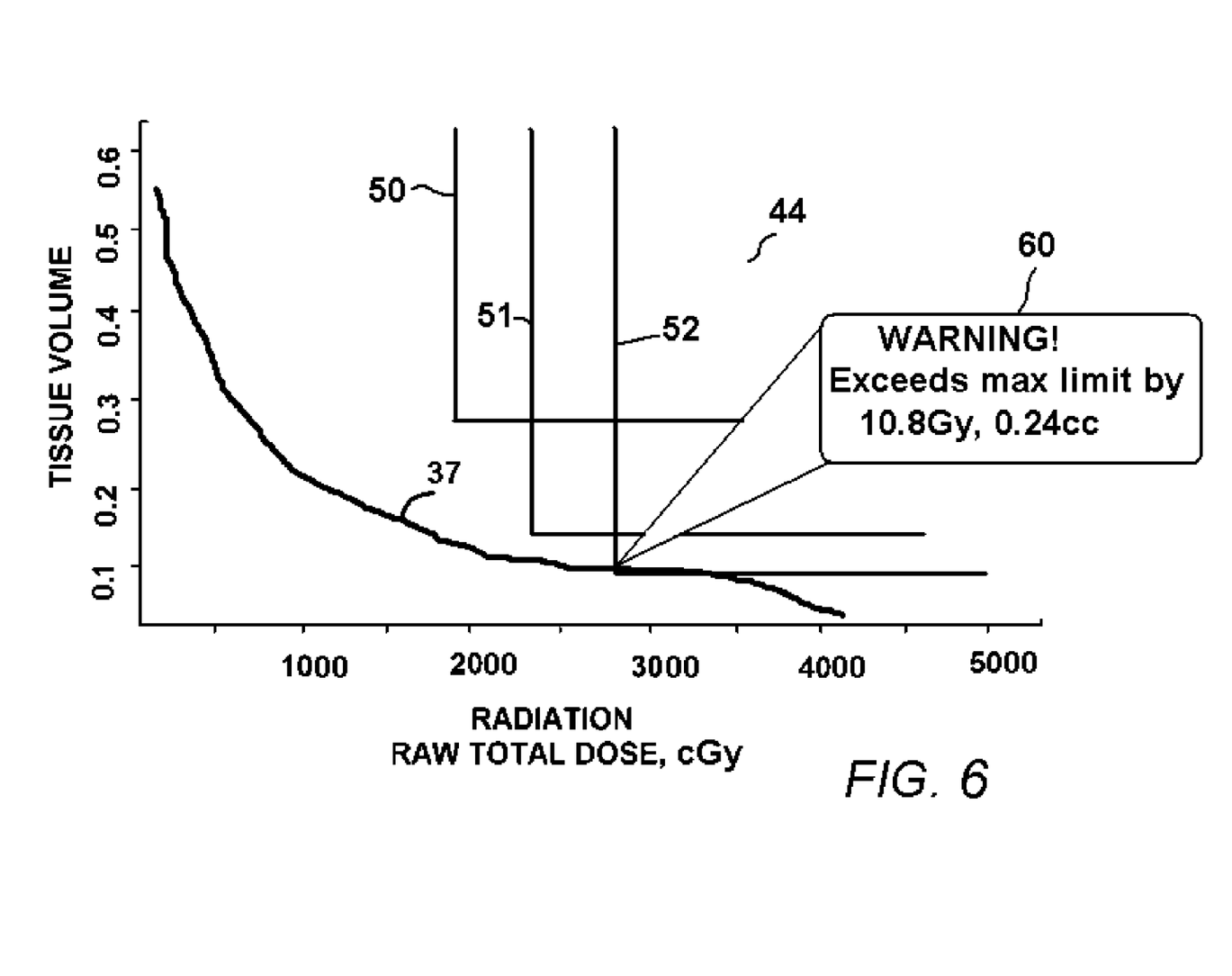
FIG. 6 shows the modified dose volume histogram of FIG. 5 combined with a system generated warning indicator.

Referring to FIG. 6, an exemplary warning indicator 60 is shown. The warning indicator 60 is graphical in nature and presents, in text, the dosage details that exceed the acceptable threshold 52. The warning indicator 60 can be accompanied by other auxiliary visual and/or audible warning indicators 30, such as a flashing light and/or the sounding of a warning buzzer.

Heeding any warning that is generated with the modified dose volume histogram 44, a physician/dosimetrist can quickly ascertain if a radiation therapy plan should be altered so that it falls into the acceptable safety ranges. If the initial treatment plan results in radiation dosages that are dangerous, a new treatment plan is created and the analysis is repeated. See loop arm 62 in FIG. 4.

Likewise, by referencing the modified dose volume histogram 44, a physician/dosimetrist can determine if a more aggressive course of radiation can or should be used. The information is graphically conveyed to the physician and can be instantly recognized by glancing at the modified dose volume histogram.

It will be understood that the embodiment of the present invention that is illustrated and described is merely exemplary and that a person skilled in the art can make many variations to those embodiments. All such embodiments are intended to be included within the scope of the present invention as defined by the claims.

What is claimed is:

1. A method of warning when a planned dose of radiation will exceed a predetermined limit, said method comprising the steps of:
   imaging a tissue mass to obtain imaged data that identifies abnormal tissue that require radiation therapy and normal tissue that radiation therapy should attempt to avoid;
   utilizing a system computer to access reference databases that contain dose tolerance limits for said tissue mass;
   utilizing an electronic display;
   generating a dose volume histogram that plots at least some of said imaged data versus proposed doses of radiation, wherein said dose volume histogram presents a data curve that is displayed on said electronic display;
   recalling at least one dose tolerance limit from at least one of said reference databases for said tissue mass;
   displaying said at least one dose tolerance limit on said display with said data curve to produce a modified dose volume histogram;
   analyzing said at least one dose tolerance limit and said data curve with said system computer to determine if said data curve surpasses said at least one dose tolerance limit at any point along said data curve; and
   automatically generating a visual warning indicator on said electronic display should said data curve surpass said at least one dose tolerance limit at any point along said data curve.

2. The method according to claim 1, further including the step of selecting a plotting format, from a plurality of possible formats, for at least one dose tolerance limit retrieved from at least one of said reference databases.

3. The method according to claim 2, wherein said step of displaying said at least one dose tolerance limit on said display includes plotting said at least one dose tolerance limit in said plotting format selected.

4. The method according to claim 2, wherein said plurality of possible formats includes a first format where said volume of said normal tissue is plotted against a first radiation dose level.

5. The method according to claim 2, wherein said plurality of possible formats includes a second format where a percentage of said volume of said normal tissue is plotted against a second radiation dose level.

6. The method according to claim 2, wherein said plurality of possible formats includes a third format where a percentage of said volume of said normal tissue that is equal to zero is plotted against a third radiation dose level.

7. A method of determining radiation levels for use during radiation therapy for a subject patient, said method comprising the steps of:
   imaging a volume of tissue within said subject patient to be affected by said radiation therapy, therein obtaining imaging data;
   computing a proposed radiation treatment plan for said subject patient using said imaging data;
   generating a dose volume histogram in a system computer using said proposed radiation treatment plan and said imaging data, wherein said dose volume histogram presents a data curve;
   utilizing a display that is coupled to said system computer;
   displaying said data curve and said dose tolerance limits on said display to create a modified dose volume histogram;
   comparing said data curve to dose tolerance limits with said system computer;
   having said system computer automatically generate a visual warning on said display should said data curve surpass said dose tolerance limits at any point along said data curve.

8. The method according to claim 7, further including the step of recalling said dose tolerance limits from at least one of reference databases accessed by said system computer.

9. The method according to claim 8, further including the step of selecting plotting formats for said dose tolerance limits.

10. The method according to claim 8, wherein said step of plotting said dose tolerance limits onto said dose volume histogram includes plotting said dose tolerance limits in said plotting formats selected.

11. The method according to claim 9, wherein said plotting formats include a first format where said volume of said tissue is plotted against a first radiation dose level.

12. The method according to claim 11, wherein said plotting formats include a second format where a percentage of said volume of said tissue is plotted against a second radiation dose level.

13. The method according to claim 12, wherein said plotting formats include a third format where a percentage of said volume of tissue that is equal to zero is plotted against a third radiation dose level.

14. A method of producing a reference graph for use in selecting radiation levels to be used during radiation therapy for a subject patient, said method comprising the steps of:
- identifying a volume of tissue within said subject patient to be affected by said radiation therapy;
- generating a dose volume histogram that plots at least some of said volume of tissue versus proposed doses of radiation, wherein said dose volume histogram presents a data curve;
- displaying said dose volume histogram and said dose tolerance limits on an electronic display, wherein said dose tolerance limits are overlaid onto said dose volume histogram; and
- overlaying a warning on said electronic display that visually indicates where said data curve surpasses said dose tolerance limits should said data curve surpass said dose tolerance limits at any point along said data curve.

\* \* \* \* \*